US005545719A

United States Patent [19]
Shashoua

[11] Patent Number: 5,545,719
[45] Date of Patent: Aug. 13, 1996

[54] NERVE GROWTH PEPTIDES

[75] Inventor: Victor E. Shashoua, Brookline, Mass.

[73] Assignee: Neuromedica, Inc., Cambridge, Mass.

[21] Appl. No.: 201,046

[22] Filed: Feb. 24, 1994

Related U.S. Application Data

[63] Continuation of Ser. No. 700,653, May 14, 1991, abandoned, which is a continuation-in-part of Ser. No. 517,159, May 1, 1990, abandoned.

[51] Int. Cl.$^6$ .............................. C07K 7/00; C07K 7/06; C07K 7/08; C07K 9/00
[52] U.S. Cl. ..................... 530/345; 530/326; 530/327; 530/328; 530/329; 530/330
[58] Field of Search ................................. 530/324–330, 530/345, 399, 402; 514/2, 12–17

[56] References Cited

U.S. PATENT DOCUMENTS

| | | | |
|---|---|---|---|
| 4,185,095 | 1/1980 | Young | 424/177 |
| 4,287,184 | 9/1981 | Young | 424/177 |
| 4,407,744 | 10/1983 | Young | 260/112 R |
| 4,550,109 | 10/1985 | Folkers et al. | 514/249 |
| 4,868,161 | 9/1989 | Roberts | 514/49 |
| 4,902,505 | 2/1990 | Pardridge et al. | 424/85.7 |
| 4,933,324 | 6/1990 | Shashoua | 514/549 |
| 4,939,174 | 7/1990 | Shashoua | 514/549 |
| 5,068,224 | 11/1991 | Fryklund et al. | 514/21 |
| 5,112,596 | 5/1992 | Malfroy-Camine | 424/2 |
| 5,169,762 | 12/1992 | Gray et al. | 435/69.1 |
| 5,169,764 | 12/1992 | Shooter et al. | 435/69.7 |

FOREIGN PATENT DOCUMENTS

| | | |
|---|---|---|
| 30009 | 6/1981 | European Pat. Off. . |
| 91694 | 10/1983 | European Pat. Off. . |
| 8500520 | 2/1985 | WIPO . |
| 8907938 | 9/1989 | WIPO . |

OTHER PUBLICATIONS

Jacob, et al., J. Med. Chem, vol. 28, pp. 106–110 (1985).
Scott et al, Nature, 302, 538–540, 1983.
Shashoua, et al, Brain Research, 522 181–190 (1990).
Young, S. W. et al., FEBS Letters, 338: 212–216, 1994.
Leonard, D. G. B. et al., Molecular and Cellular Biology, 7(9): 3156–67, 1987.
Shea, T. B. et al., Developmental Brain Research, 21: 307–314, 1985.
V. E. Shashoua, "The role of ependymin in the development of long lasting synaptic changes", J. Physiol. Paris, 83:232–239 (1988–1989).
Y. Makino et al., "Pharmaceuticals Permeable To Blood–Brain Barrier", Chemical Abstracts, vol. 106, No. 12, issued 23 Mar. 1987.
G. Dhopeshwarkar et al., "Fatty Acid Transport Into The Brain", Biochim. Biophys. Acta 1972, 255(2), 572–9.
R. Spector, "Fatty Acid Transport Through the Blood–Brain Barrier", J. Neurochem. 1988, 50(2), 639–43 (Eng).
V. E. Shashoua et al., "γ-Aminobutyric Acid Esters.1. Synthesis, ..." Journal of Medicinal Chemistry, vol. 27, No. 5, pp. 659–664 (1984).

J. N. Jacob et al., "γ-Aminobutyric Acid Esters.2.Synthesis, ...", Journal of Medicinal Chemistry, vol. 28, No. 1, pp. 106–110 (1985).
G. W. Hesse et al., "Inhibitory Effect of Cholesteryl ...", Neuropharmacology, vol. 24, No. 2, pp. 139–146 (1985).
J. Scott et al., "Isolation and nucleotide sequence of a cDNA encoding ...", Nature, 302: 538–540 (7 Apr. 1983).
V. E. Shashoua, "The Role of Brain Extracellular Proteins ...", Cellular and Mol. Neurobiol., 5 (1/2):183–207 (1985).
R. Meier et al., "Molecular Cloning of Bovine and Chick Nerve Growth (NGF) ...", The EMBO Journal, vol. 5, 7:1489–1493 (1986).
A. Konigstorfer et al., "Molecular Characterization Of An Ependymin Precursor from Goldfish Brain", J. Neurochem., 52:310–312 (1989).
A. Konigstorfer et al., "Biosynthesis of Ependymins from Goldfish Brain", J. Biol. Chem., vol. 264 (23): 13689–13692 (1989).
M. Rocco et al., "Models of Fibronectin", The EMBO Journal, 6: 2343–2349 (1987).
T. Higuchi et al., "Prodrugs as Novel Drug Delivery Systems," American Chem. Society, ACS Symposium Series, vol. 14, pp. 14–15 (1975).
S. Iwakami et al., "Inhibition of Arachidonate 5-Lipoxygenase by Phenolic Compounds," Chem. Pharm. Bull. (Japan), 34(9), 3960–3963, (1986).
I. Yamatsu et al., Chemical Abstracts, vol. 100, No. 19, issued 7 May 1984, "Polyprenyl Carboxylic Acid Amides.".
G. Bourat et al., "Long Chain Esters of Pipotiazine as Long–Acting Psychotropic Pro–Drugs," pp. 105–114.
K. A. Jacobson et al., "Adenosine analogs with covalently attached lipids ...", FEBS LETTERS, vol. 225, Nos. 1,2 pp. 97–102 (Dec. 1987).
A. Garzon– Aburbeh et al., "A lymphotropic Prodrug of L–Dopa: Synthesis," J. Med. Chem. 29;687–691 (1986).
U. K. Mazumdar & D. C. Day, "Preparation and Evaluation of Ethambutol Derivatives," Indian J. Pharm. Sci. 47(6) :179–180 (1985).
V. E. Shashoua, "Ependymin, a B rain Extracellular Glycoprotein, and CNS Plasticity," reprinted from Activity–Driven CNS Changes in Learning and Development, vol. 627 of the Annals of the New York Academy of Sciences, Aug. 5, 1991 ).

Primary Examiner—Marianne P. Allen
Attorney, Agent, or Firm—Wolf, Greenfield and Sacks, P.C.

[57] ABSTRACT

This invention describes novel molecules capable of promoting nerve growth, and therapeutic methods for promoting nerve growth using these molecules. Molecules of this invention include a protein fragment substantially homologous to an active region of the brain glycoprotein ependymin. The active region is primarily responsible to the nerve growth promoting capacity of these molecules. The molecules of this invention may be administered to a subject to correct genetic and systemic disorders and to treat nervous systems disorders resulting from trauma.

7 Claims, 2 Drawing Sheets

NERVE GROWTH PEPTIDES

GOVERNMENT SUPPORT

The invention described herein was supported in part by a grant from the National Institutes of Health.

This application is a continuation application under 37 C.F.R. 1.62 of prior application Ser. No. 07/700,653, filed on May 14, 1991, now abandoned, which was a continuation-in-part of application Ser. No. 07/517,159, filed May 1, 1990 entitled "Nerve Growth Peptides and Uses Therefor", now abandoned the entire disclosure of which is incorporated herein by reference.

TECHNICAL FIELD

This invention is in the field of neurobiology and neurochemistry.

BACKGROUND

The survival, growth, maintenance and function of certain classes of nerve cells during development are believed to depend on nerve growth factors. A molecule that functions as a nerve growth factor is ependymin.

Ependymin is a glycoprotein that is synthesized in the brain by specific cells which secrete and maintain a steady-state concentration of the protein in the brain extracellular (ECF) and cerebrospinal (CSF) fluids. Ependymin comprises dimers of two polypeptide chains (alpha, M.W. 37,000 and beta, M.W. 31,000) linked by disulfide bonds. These are converted to the gamma-chain (M.W. 26,000) in ECF. The amino acid sequences of the alpha, beta and gamma chains are substantially identical. Ependymins are initially released into the extracellular spaces of the brain as mixtures of $\alpha\beta$ dimers (M.W. 68,000) which become converted to $\beta\gamma$ (M.W. 58,000) and $\gamma_2$ (M.W. 53,000) dimers. Shashoua, V. E., *J.Physiol.* (Paris) 83:232–329 (1989). The mode by which ependymin functions as a nerve growth promoter is not known. Ependymin has been implicated in the consolidation process of long-term memory formation. V. E. Shashoua, *Cell. Molec. Neurobiol.*, 5:183–207 (1985).

For nerve growth factors to be therapeutically useful, they must be delivered to an active site in the body. This requirement is beset with several difficulties. First, although many nerve growth factors are peptides, P. L. McGeer et al., "Molecular Neurobiology of the Mammalian Brain", 2nd Edition, Plenum Press, 1987, the particular amino acid sequences responsible for their nerve growth-promoting properties are either unknown or are poorly characterized.

Second, ingestion of a drug containing a nerve growth factor often is not possible because many drugs will not survive the environment of the stomach. Thus, easy and safe self-administration of many drugs is not available. A drug, of course, can be injected directly into the bloodstream of the patient. However, because some drugs do not survive for very long in the bloodstream, frequent injections may be necessary, at great inconvenience to the patient. The inability of a drug to survive in the bloodstream can also be overcome in certain instances by increasing the dosage. Unfortunately, increasing the dosage can result in undesireable side effects.

The delivery of a nerve growth factor such as ependymin into the central nervous system (CNS) via the bloodstream involves an additional and extraordinary obstacle; the nerve growth factor must be capable of crossing the blood-brain barrier. The blood-brain barrier may be regarded as a biological exclusion barrier involving both passive and active transport, the barrier controlling the exchange of materials between the plasma and the central nervous system. Many drug substances, including ependymin, are unable to pass through this barrier in efficacious amounts, or at all. Therefore, attempts to increase the level of ependymin in the central nervous system by introducing it into the bloodstream are not successful because it does not cross the blood-brain barrier. Therefore, it would be useful to develop molecules having the same, or greater, activity as ependymin that could be adapted easily to be introduced into the central nervous system.

SUMMARY OF THE INVENTION

The invention provides novel molecules that are protein fragments capable of stimulating nerve growth. The protein fragments correspond to amino acid sequences of naturally-occurring proteins and are no greater than about 80 amino acids in length. Proteins from which the nerve growth stimulating fragments are derived include neuronotrophic proteins such as epidermal growth factor, tubulin, nerve growth factor (NGF), laminin, fibronectin, NCAM and ependymin.

The protein fragments are preferably about 16 amino acids in length and contain sequences substantially homologous with one or more active regions of ependymin. Active regions of ependymin include amino acid sequences of from 5 to about 8 amino acid residues. These sequences of the ependymin active regions are located within two, non-contiguous neuroactive domains of ependymin. Active regions are associated with the N-terminal domain of the ependymin chain, particularly the first eighty amino acid residues. Active regions are also associated with the C-terminal domain of ependymin, in particular between amino acid residues 130 and 195. Preferably, the protein fragments contain sequences that are between about 70% and 100% homologous with the respective active region sequences of ependymin.

A preferred embodiment of the invention is an ependymin fragment containing amino acids from an active region of an ependymin neuroactive domain, the fragment having a sequence substantially homologous to at least one protein fragment other than ependymin. The protein fragment-sequences substantially homologous with ependymin active region sequences are primarily responsible for the nerve growth stimulating properties of the protein fragments.

The protein fragments of the invention can also be coupled to one or more secondary molecules, which molecule can include a second protein fragment derived from the original protein and/or from another protein. The ependymin fragment of the preferred embodiment can be coupled to one or more secondary molecules which can be either amino acid sequences from another ependymin fragment, sequences from a separate protein, or a non-proteinaceous moiety.

A preferred secondary molecule of the present invention is a pharmaceutically acceptable carrier whose linkage to the protein fragment is not degraded in the environment of the stomach and the bloodstream and, therefore, can be administered orally. The carrier also passes readily through the blood-brain barrier delivering the protein fragments of this invention into the central nervous system. The combination of protein fragment and carrier is called a prodrug. Prodrugs are formed by chemically linking a suitable non-proteinaceous carrier to the protein fragments of the invention, the carrier being selected such that it has a brain penetration index of at least two times the brain penetration index of the protein fragment alone. Upon entering the central nervous system, prodrug can remain intact or the chemical linkage between the carrier and the protein fragment may be hydrolyzed, thereby separating the carrier from the fragment to release the nerve growth-stimulating fragment. The carrier preferably is a normal component of the central nervous system and is inactive and harmless. The preferred carriers are fatty acids, cholesterol, and glucose derivatives.

The present invention also discloses therapeutic methods for promoting nerve growth using the protein fragments of this invention. The methods include administering to a patient a protein fragment having a sequence that is substantially homologous to an active region of a neuroactive domain of ependymin. An embodiment of the method of the present invention uses sustained release delivery systems to administer the protein fragment(s) into the blood stream or a target tissue.

Through use of the compositions and methods of the present invention, nerve growth can be modulated to correct genetic and systemic disorders and to treat nervous system disorders resulting from trauma.

BRIEF DESCRIPTION OF THE DRAWINGS

FIG. 3(A–C) are graphs showing the effect of a peptide fragment including the sequence ETLQFR (SEQ. I.D. No. 26), and its mono- and di-docosohexaenoic acid derivative on neurite growth of neuroblastoma cells.

DETAILED DESCRIPTION OF THE INVENTION

The present invention provides protein fragments capable of promoting nerve growth. The term "promoting nerve growth" means the ability of the protein fragment to stimulate nerve sprouting, stimulate nerve elongation, and/or promote activities collateral thereto. Specifically, "collateral" activities are meant to encompass extracellular matrix formation. Extracellular matrix formation can define the locus at which changes in existing synaptic elements or growth of new synapses will take place. This extracellular matrix may provide a pathway for development of new neuronal connections. See generally, V. E. Shashoua, "The Role of Brain Extracellular Proteins in Neuroplasticity and Learning", *Cell. Mol. Neurobiol.* 5:183–207 (1985). See also P. L. McGeer et al., supra, pp. 419–420, describing neural cell adhesive molecules, or NCAM's that are instrumental in attaching outgrowing nerve fibers to extracellular matrices that guide nerve fibers to their targets.

The protein fragments of the present invention are amino acid sequences of one or more portions of a protein. The term "protein fragment" means portions substantially less than the entire naturally-occurring protein. The protein fragments preferably are no larger than about 80 amino acids long, and most preferably are between about 5 and about 16 amino acids long. The term includes protein fragments of this length and functional equivalents thereof. The term "functional equivalents" is meant to encompass any modifications in peptide bonding, deletions, and/or substitutions to the amino acid sequences, or any deletions, and/or substitutions to the nucleotide sequences that code for these amino acids, such that the protein fragment, although it may have different physical properties, is within the fragment length disclosed herein and still is capable of stimulating nerve growth.

Applicants have discovered that the protein fragments of the invention include selected amino acid sequences that are substantially homologous to one or more "active regions" of ependymin. The term "substantially homologous" is meant to include protein fragment sequences that have at least about 70% homology to a given active region. The term is therefore meant to include sequence homologies that range from about 70% homology to complete homology (100%).

These active regions have been associated with the nerve growth-promoting properties of ependymin. The protein fragments of the invention may consist of a larger peptide chain, a smaller part of which corresponds to an ependymin active region. Alternately, the fragment may correspond entirely to the active region. The "active region" is preferably a short sequence of ependymin of between about 5 and about 8 amino acids in length.

The nerve growth promoting molecules of the present invention include a polypeptide which includes the sequence ETLQFR (SEQ. I.D. No. 26) or functional equivalent thereof. Functional equivalents are meant to encompass any deletions, substitutions, and/or additions to the ETLQFR sequence, such that the polypeptide or polypeptide fragment still is capable of promoting nerve growth. The polypeptides preferably are less than 50 amino acids long. Most preferably the polypeptides are less than 15 amino acids long.

The protein fragments of the invention are substantially homologous to active regions of ependymin that are located with one or more neuroactive domains of ependymin. One neuroactive domain contains ependymin active regions that have significant effects in promoting nerve elongation and nerve sprouting. Preferred active region sequences derived from this neuroactive domain of the ependymin molecule are associated with the N-terminal region of the ependymin chain, in particular between amino acid residues 1 and 80. Proteins containing fragments thereof that are substantially homologous to active regions in this ependymin neuroactive domain include proteins such as epidermal growth factor (EGF), EGF receptor, nerve growth factor (NGF), laminin, and integrin.

Another neuroactive domain of ependymin containing active regions substantially homologous to a protein fragment has effects on extracellular matrix formation. This domain is associated with the C-terminal end of the ependymin chain, preferably between amino acids residues 130 and 195. Proteins containing fragments that are substantially homologous to active regions in this ependymin neuroactive domain include laminin, NCAM, tubulin, and fibronectin.

The preferred active regions of the ependymin neuroactive domain effective in extracellular matrix formation are shown in Table I along with the protein fragments to which these active regions are substantially homologous.

which these active regions are substantially homologous are shown as well. The proteins referred to in Tables I and II are collectively referred to hereinafter as "neuronotrophic" proteins.

TABLE I

Matrix-forming active regions of Ependymin

| I.D. Number | Ependymin active region[a] | Protein fragment (homologous segment[b]) | % Homology | Reference |
|---|---|---|---|---|
| 1 | Asp Leu Gln Val Phe Val (164–169) | Human fibronectin (886–890) | 83.3 | Kornbluth et al. EMBO J., 4:1755 (1985) |
| 2 | Gly Glu Lys Lys Asp (146–150) | Fibronectin receptor (660–664) | 100.0 | Argravos et al., J. Cell. Biol. 105, (1987) |
| 3 | Ala Thr His Glu Ser (94–98) | Tubulin (yeast 2-3) (282–286) | 100.0 | Schatz et al., Mol. Cell. Biol., 6:3711 |
| 4 | Cys Leu Pro _ Val Ser Gly (137–142) | Laminin Human B1 (1056–1062) | 71.4 | Sashi et al., PNAS, USA, 84:935 |
| 5 | Leu Pro Val Ser Gly Ser (138–143) | NCAM (197–201) | 83.3 | Dickson et al., Cell., 50:1189 |
| 6 | Pro Cys His Ala Pro Pro (6–11) | Integrin (human) (21–26) | 83.3 | Horwitz & Hynes Cell., 46:271 |

[a]Numbers in parenthesis refer to the amino acid residue number of the gamma-chain of ependymin, cited in Konigstorfer et al., J. Neurochem., 52:310–312 (1989), the first residue being number 1.
[b]Numbers refer to the amino acid residue number of the protein, the complete sequence of which is cited in the reference.

Similarly, Table II presents the preferred active regions of the ependymin neuroactive domain effective in stimulating nerve growth and elongation. The protein fragments to

TABLE II

Nerve growth active regions of Ependymin

| I.D. Number | Ependymin active region[a] | Protein fragment (homologous segment[b]) | % Homology | Reference |
|---|---|---|---|---|
| 7 | Gly Gly His Asp Leu Glu Ser Gly (23–30) | Mouse Epidermal Growth Factor (586–593) | 75 | Arundi et al., J. Biochem., 29:365 |
| 8 | Asp Asp Leu Gln _ Val Phe (163–168) | Epidermal Growth Factor (169–175) | 85.7 | Arundi et al., J. Biochem., 29:365 |
| 9 | Pro Leu Thr _ Ser Gly (11–15) | Human Epidermal Growth Factor, Receptor (691–696) | 83.3 | Gregory & Preston, Int. J. Pept. Prot. Res., 9:107 |
| 10 | Leu Ile His Phe Glu Glu Gly Val (59–66) | Human Epidermal Growth Factor (691–696) | 75.0 | Gregory & Preston, Int. J. Pept. Prot. Res., 9:107 |
| 11 | Gly Glu Phe Ser _ Tyr Asp Ser (30–36) | Nerve Growth Factor (10–15) | 75.0 | Scott et al.; Nature, 301:538 |
| 12 | His Ala _ Pro Pro Leu Thr Ser (8–14) | Nerve Growth Factor, Precursor (34–40) | 75 | Scott et al.; Nature, 301:538 |
| 13 | Asp Leu Glu Ser Gly Glu Phe (26–32) | Laminin B1 (Human and Mouse (126–131) | 71.4 | Rocco et al., EMBO J., 6:2343 |

[a]Numbers in parenthesis refer to the amino acid residue number of the gamma-chain of ependymin, cited as in Table I.
[b]Numbers refer to the amino acid residue number of the protein, the complete sequence of which is cited in the reference.

The protein fragments of the invention can include fragments that are substantially homologous with functional equivalents of the active regions. As described above, the resulting protein fragments may have different physical properties but still are capable of promoting nerve growth as defined herein. For example, preferred protein fragments substantially homologous to the active region between amino acid 30 and amino acid 36 of the ependymin molecule (Table II: sequence I.D. No. 11) can include, but are not limited to, fragments homologous to amino acid sequences such as sequence I.D. numbers 14 and 15.

The protein fragments of the invention are characterized in having one or more structural forms. In one embodiment, the protein fragments of the invention consist of fragments entirely (100%) homologous to ependymin active regions. These fragments include, but are not limited to, fragments identical to the amino acid sequences of ependymin referred to in Tables I and II as well as any functional equivalents of these active regions.

In another embodiment, the fragments are coupled at either or both of their N-terminal or C-terminal ends to other molecules, referred to herein as secondary molecules. These secondary molecules can be portions from the same protein as the original protein fragment, from a completely different protein, or from a non-proteinaceous moiety. The fragment can be coupled to one or more secondary molecules via a group capable of being attached, directly or indirectly, to a carboxyl group of the secondary molecule. The carboxyl group of a secondary molecule can form, for example, an ester or amide bond with the nerve growth-stimulating protein fragment. Other couplings such as phosphoramide, sulfate, sulfonate, peptide, phosphate or urethane can be used to couple the secondary molecule to the protein fragment as will be recognized by one of ordinary skill in the art.

The secondary molecule can be a segment of the protein fragment contiguous with the original protein fragment. The term "contiguous" means that the secondary molecule is derived from an adjacent portion of the original protein fragment. Since the protein fragment is substantially homologous to an ependymin active region within an ependymin neuroactive domain, a protein fragment substantially homologous to an active region of one ependymin domain, for example in Table I, can be coupled to a secondary molecule taken from a contiguous portion of the same neuroactive domain.

In embodiments of this type, therefore, a protein fragment substantially homologous with a first active region of ependymin is preferably linked at either or both of its N-terminal and C-terminal ends to a secondary molecule substantially homologous to that portion of ependymin that is adjacent to, or closely associated with, the first active region. Referring to Table II, for example, a protein fragment of this type can include a fragment substantially homologous with active region sequence ID number 11 (amino acid residue 30 to amino acid residue 36) peptide bonded to a protein fragment substantially homologous to the portion of ependymin that is on either side of the active region (e.g. amino acid residues 23 to 29 and/or amino acid residues 37 to 43). Examples of this embodiment are sequence I.D. numbers 19 through 25. In particular, sequence I.D. number 19 is amino acid residue 23 to 29 of ependymin, sequence I.D. number 20 is a functional equivalent thereof, and sequence I.D. numbers 21–25 are protein fragments in which these sequences are peptide bonded to their adjacent active region.

The secondary molecule can also be derived from a non-contiguous portion of the original fragment, i.e. a non-adjacent portion, so that the respective fragments are substantially homologous with active regions from different neuroactive domains of ependymin. Referring to Tables I and II, for example, a protein fragment of this type can include a fragment substantially homologous with active region sequence ID number 11 (amino acid residue 30 to amino acid residue 36) peptide bonded at either or both of its N-terminal and C-terminal ends to a protein fragment substantially homologous to active region sequence number 1 (amino acid residue 164 to amino acid residue 169). In this embodiment, the secondary molecule is a protein fragment derived from a different neuronotrophic protein than the original protein fragment.

In further embodiments of the invention, protein fragments substantially homologous with active regions derived from a neuroactive domain of ependymin can be coupled to a secondary molecule that is derived from a completely different protein that may not possess nerve growth stimulating properties. For example, a protein fragment can be coupled to a secondary molecule that is capable of targeting a specific nerve cell or nerve-innervated tissue within the body. Secondary molecules of this type may include, for example, tissue-specific proteins (e.g. neuron-specific enolase; PCP 9.5: Wilkinson et al., *Science* 246:670 (1989)) or tissue or cell specific antibodies (e.g. neuron-specific monoclonal antibodies: Klose, M. and D. Bentley, Science 245:982 (1989)).

Molecules of this invention also include one or more protein fragments that can be coupled, or otherwise bound to, a secondary molecule that is a carrier capable of delivering the fragment across the blood-brain barrier and effectively delivering the protein fragment of this invention to the central nervous system. The combination of a secondary molecule capable of crossing the blood-brain barrier and protein fragment(s) of this invention is referred to as a "prodrug".

Preferred secondary molecules useful in forming prodrugs are non-proteinaceous and are disclosed in co-pending U.S. applications Ser. Nos. 160,667 and 315,134, the disclosures of which are incorporated herein by reference. Such secondary molecules may be linked to the protein fragment(s) by chemical linkages that are hydrolyzed by enzymes in the central nervous system. In this way, the prodrug can cross the blood-brain barrier and can liberate the protein fragment of this invention by, for example, hydrolysis of the linkage between the secondary molecule and protein fragment. The non-toxic secondary molecule is then free to remain intact or be further metabolized by the brain. Alternately, it may not be necessary to release the protein fragment from its secondary molecule in order to obtain the desired results. Under these circumstances, the prodrug can cross the blood-brain barrier and remains intact.

The preferred carriers of the invention are capable of delivering the nerve-growth promoting protein fragment across the blood-brain barrier in an efficient manner. A brain penetration index (BPI) determination is a useful criterion for measuring the capacity of a molecule to efficiently cross the blood-brain barrier. Shashoua, V. E., Jacob, J. N., Ridge, R., Campbell, A. and Baldessarini, R. J., *J. Med. Chem.* 27, 659 (1984). The BPI is a measure of the uptake of a compound by the brain relative to its uptake by the liver. The liver is chosen as a reference since it is an organ which presents no barrier to diffusable molecules present in the blood. The amount of material in the liver will reflect the amount available rather than the initial dose injected. Preferred carriers of the invention have a BPI at least twice that of the nerve growth promoting polypeptides.

Determination of the BPI is made by measuring the quantity of the compound (e.g. secondary molecule or polypeptide) present in the brain and liver 5 minutes after a subcutaneous injection, the equation being: BPI=[brain]/[liver]×100.

For these measurements, $^{14}$C-labelled peptides and secondary molecules can be synthesized (see e.g. Sigma® Radiochemicals R Catalogue-Sigma® Chemical Co., St. Louis, Mo. 63178), dissolved in 15% propylene glycol in 0.1M NaHCO$_3$, and then injected subcutaneously (S.C.) into male balb C mice (20±2 g). After 5 minutes, the animals are sacrificed by cervical fracture and the brain and liver dissected out, weighed and homogenized in 8 and 10 ml, respectively, of Brain Protein Solvent (BPS) buffer [BPS= 2% sodium dodecyl sulphate in 0.03M Tris, 6M urea, (pH 7.6), 0.01M EDTA and 0.14N NaCl]. Aliquots can then be counted for $^{14}$C content in 10 ml of a liquid scintillation fluid (Liquiscent-National Diagnostic Co., Somerville, N.J.) using a Beckman liquid scintillation counter. The $^{14}$C counts are then used to calculate the total quantity of the compound present in the brain per gram of tissue as compared to that in the liver. The ratio of the amount in the brain as a percent of that present in the liver is determined.

The preferred carrier can be a fatty acid which has between about 16 and about 26 carbon atoms, and more preferably between about 20 and about 24 carbon atoms. A particularly preferred fatty acid is docosohexa-enoic acid (DHA). Synthesis of DHA anhydride and coupling of DHA anhydride to a protein fragment derived from the nerve growth promoting region of gamma-ependymin are described in the example.

The length, the degree of saturation, and the extent to which the fatty acid is naturally occurring in the brain all effect the ability of the fatty acid to deliver the nerve-growth promoting polypeptide across the blood-brain barrier to an active site in the brain.

Fatty acids which are partially unsaturated and occur naturally in the brain are particularly preferred as secondary molecules (i.e. carriers). Fatty acids which occur naturally in the brain include those with 16 carbon atoms and 0, 1 or 2 double bonds (C16:0; C16:1; and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5; and C22:6). The position of the double bonds can be between any of the carbon atoms and the fatty acids, the preferred loci being those which occur naturally in the fatty acids of the central nervous system. The C16:0 and C22:6 are the preferred fatty acid carriers due to their preference for concentrating in the synaptosomal membrane, with C22:6 being most preferred. It also has been found that C18:3 acts above average in its ability to deliver a compound across the blood-brain barrier.

Branched chain fatty acids having between 16 and 26 carbon atoms can also be used within the present invention. A hydrogen atom of the foregoing fatty acids can be replaced with a methyl, ethyl or isopropyl substituent at various positions along the carbon chain. Other, examples include the naturally occurring polyisoprenoids (dolicols) and analogs thereof. Other secondary molecules besides fatty acids capable of introducing the nerve growth-promoting molecule across the blood-brain barrier include inositol, 1–4 dihydropyridine, cholesterol, glucose and glucose derivatives. Preferred glucose derivatives are glucose esters such as 3-glucose succinoyl esters.

The preferred bonds for coupling secondary molecules to the protein fragments are those capable of surviving the environment of the stomach, thereby allowing oral administration of the prodrug. The preferred bonds also hydrolyze when the prodrug is introduced into the brain. An example of such a bond is believed to be an amide bond. The bonds incapable of surviving the environment of the stomach, e.g. ester bond, or also may be used to link the secondary molecule to the protein fragment. Prodrugs coupled with bonds such as these can be injected or protected from the environment of the stomach using coatings or liposomes, for example. Those skilled in the art would know how to coat such compounds for this purpose. Such a coating may be called for even in the presence of an amide bond between the carrier and the nerve growth factor.

The preferred method for facilitating bond coupling of the secondary molecules to the protein fragments of the invention is through one or more basic amino acids. These basic amino acids are preferably lysine and arginine. These amino acids can be part of the basic amino acid side chains of the protein fragments of this invention shown, for example, in sequence I.D. numbers 2 and 17. Alternately, these basic amino acids are not part of the original protein fragment and can be peptide bonded to the N-terminal end of the fragment and/or the C-terminal terminal end of the fragment.

Various combinations of lysine and arginine can be employed to couple fragments of the invention with secondary molecules. Particularly preferred combinations of these basic amino acids include a pair of lysine residues bonded to the N-terminal end and/or the C-terminal end of the protein fragment; a single arginine residue bonded to the C-terminal end of the fragment; an arginine residue bonded to the N-terminal end of the fragment, which residue is bonded to a lysine; an arginine residue bonded to the C-terminal end of the fragment, which arginine residue is bonded to a lysine; and a single lysine residue bonded to the C-terminal end of the fragment.

An N-terminal lysine residue, in particular, has two amino groups with which a secondary molecule can form a bond. Thus, two terminal lysine residues that are peptide bonded to a fragment of the invention have a total of three amino groups with which a secondary molecule can form a bond: one N-terminal amino group of the fragment and two coupling sites available on the γ carbon of each lysine residue. A mono-substituted protein fragment (Lys-Lys) derivative can have a secondary molecule linked to either one of the three available amino groups, or it can be a mixture of all three forms with the average composition of a mono-substituent. A di-substituted protein fragment can be a mixture of all possible substitutions on 2 out of the 3 available sites. Because enzymes exist that hydrolyze the peptide bonds between the two lysines and the rest of the molecule, the growth-promoting protein may be liberated from the prodrug. In yet another embodiment of the invention, the secondary molecule may be coupled to the end of the peptide fragment through an amidated C-terminal carboxyl group (—CONH$_2$).

In a preferred embodiment, the nerve growth promoting polypeptide includes the sequence KKETLQFR (SEQ. I.D. No. 27) or ETLQLRKK (SEQ. I.D. No. 28). This sequence includes the nerve-growth promoting portion ETLQFR (SEQ. I.D. No. 26) as well as two lysines (K). The peptide KKETLQFR (SEQ. I.D. No. 27) has three amino groups with which a secondary molecule can form a peptide bond: one N-terminal amino group and two gamma-amino groups of the lysine (K) moiety. These coupling sites are available for attaching the nerve growth promoting portion to secondary molecules, such as carriers capable of crossing the blood brain barrier.

The protein fragment alone, or combined with a secondary molecule, is administered to a subject in a pharmaceutically acceptable amount. Alternately, a plurality of protein fragments, either alone or combined with secondary molecules, can be administered as a "cocktail" in a pharmaceutically acceptable amount. The term "subject" is intended to include mammals. The terms "pharmaceutically acceptable amount" is that amount which is capable of promoting nerve growth in the subject. A pharmaceutically acceptable amount can be determined on an individual basis and will be based, at least in part, on consideration of the subject's size, severity of the symptoms to be treated, results sought, and specific secondary molecule used. Thus, a pharmaceutically acceptable amount can be determined by one of ordinary skill in the art employing such factors and using no more than routine experimentation.

The molecules containing protein fragments of this invention may be used in vivo to treat peripheral or central nervous system nerve injury. By "nerve injury" is meant nerve damage caused by disease and/or physical or chemical trauma, including diseases such as Huntington's, Parkinson's, and Alzheimer's. The term is also meant to include other situations wherein nerve growth is to be facilitated. For example, the protein fragments may be useful in connection with the transplantation of healthy nerve tissue to a site of nerve injury. Pre-treatment of nerve tissue with molecules of this invention or transplantation in the presence of these molecules is likely to enhance nerve connectivity and growth.

Administration of the therapeutic molecules of this invention may be made by any method which allows the protein fragment to reach the target site of nerve injury. Typical methods include oral, rectal, peritoneal, subcutaneous, intravenous and topical administration of the compounds. When the compounds are administered orally, the composition can be in the form of dragees, tablets, syrups or ampules. When the compounds are administered rectally, the composition can be in the form of a suppository. When the compounds of the invention are to be administered by topical application, they can be in the form of a gel. Physiologically acceptable vehicles for the therapeutic compositions of this invention include water, or aqueous solutions of non-toxic salts, such as saline or phosphate-buffered saline. Adjuvants, such as aluminum hydroxide gel, can also be employed. Also suitable are oil-in-water emulsions and compositions including organic solvents, such as dimethylsulfoxide (DMSO), propylene glycol, and glycerol. Solid materials can include nutritive materials such as sucrose or gelatin.

Other delivery systems can include sustained release delivery systems. Preferred sustained release delivery systems are those which can provide for release of the protein fragments of the invention in sustained release pellets or capsules. Many types of sustained release delivery systems are available. These include, but are not limited to: (a) erosional systems in which the protein fragment is contained in a form within a matrix, found in U.S. Pat. Nos. 4,452,775 (Kent) and 4,667,014 (Nestor et al.), the entire disclosures of which are incorporated herein by reference; and (b) diffusional systems in which an active component permeates at a controlled rate through a polymer, found in U.S. Pat. Nos. 3,832,252 (Higuchi et al.) and 3,854,480 (Zaffaroni), the entire disclosures of which are incorporated herein by reference.

Methods of preparing the protein fragments of this invention include isolating the alpha, beta and gamma forms of ependymin from brain tissue and preparing an enzyme digest thereof. See V. E. Shashoua, *Neurochemical Research*, 13:649–655 (1988). Individual peptide chains can be separated chromatographically. Shashoua, V. E. *Brain Res.* 122: 113–124 (1977).

Detailed sequence analysis of whole ependymin has been performed (Konigstorfer et al., *J. Neurochem.*, 52:310–312 (1989). Sequence analysis on selected proteolytic digests of the ependymin chains can also be performed using routine methods. Briefly, alpha, beta or gamma-ependymin is subject to proteolysis and the digest is separated chromatographically. Selected digests of these chains, including the neuroactive domains are sequenced using routine methods. The entire amino acid sequences of many naturally occurring neuronotrophic proteins are by now well known (see references in Tables I and II, the citations of which are incorporated herein by reference). The sequences derived from ependymin digests can be compared with known sequences from a wide variety of neuronotrophic proteins using computer database analysis.

Protein fragments and functional equivalents thereof that are identified as being substantially homologous with one or more active regions of a neuroactive domain of ependymin are preferably homologous with active regions derived from the gamma-chain of ependymin. These preferred fragments, can be synthesized using an appropriate solid state synthetic procedure. J. M. Steward and F. D. Young, *Solid Phase Peptide Synthesis*, Freemantle, San Francisco, Calif. (1968). A preferred method is the Merrifield process. Merrifield, *Recent Progress in Hormone Res.* 23:451 (1967).

Further methods of preparing the fragments of this invention include well-known recombinant DNA methods. These methods comprise synthesizing the nucleic acids encoding the fragments of the invention, incorporating such nucleic acids via suitable cloning vectors into host cells and expressing the resulting polypeptides. T. Maniatis et al., *Molecular Cloning: A Laboratory Manual*, Cold Spring Harbor Laboratory, 1982.

It will be appreciated by those skilled in the art that methods of preparing the protein fragments of this invention would also include preparing enzyme digests of other neuronotrophic proteins besides ependymin. Sequence analysis of proteolytic digests of these other neuronotrophic proteins and sequencing thereof, can be performed and the sequences derived from these neuronotrophic proteins can be compared with known ependymin sequences using computer database analysis.

This invention will now be illustrated by the following examples.

Example 1. Isolation and sequencing of gamma-ependymin and gamma-ependymin peptide fragments Ependymin was isolated from goldfish brain as previously described. V. E. Shashoua, *Neurochem. Res.* 13:649–655 (1988). Briefly, this method comprises isolating an ependymin-rich protein fraction of brain extracellular fluid by extracting brain tissue for 30 minutes at 0° C. in a buffer consisting of sodium chloride, calcium acetate in Tris (pH 7.4) and L-1-tosylamide-2-phenylethylchloromethyl ketone as a protease and esterase inhibitor, V. E. Shashoua, *Neurochem. Res.* 6:1129–1147 (1981). The gamma form of the protein was obtained by treating preparations of alpha and beta protein with peptide N-glyconase F as previously described. Shashoua, V. E. *Brain Res.* 122:113–124 (1977). The polypeptide chains, after reduction by heating for 1 min. at 95° C. in the presence of 1% beta-mercaptoethanol and 1% sodium dodecyl sulfate (SDS) in Laemmli buffer, were separated by SDS gel electrophoresis and electroblotted onto polyvinylidene fluoride membranes (Millipore Co., Bedford Mass.). After localization by Coomassie Blue staining, the bands were cut out and analysed for their N-terminal amino acid sequences using the Edman degradation and gas phase methods. Matsudaira, P., *J. Biol. Chem.*, 262: 10035–10038.

The gamma-polypeptide chain was also electroblotted onto nitrocellulose membranes. These were cut out and treated with trypsin, chymotrypsin, or *S. aureus* protease to generate peptide fragments. Aebersold, R. H. et al., *Proc. Natl. Acad. Sci, USA* 84:6970–6974 (1987). Each digest was separated by high pressure liquid chromatography into separate peptide fragments and detailed sequence analysis was performed using an Applied Biosystems model 470 sequencer (Microchemistry Laboratory, Dep't. Biology; Harvard College, Cambride, Mass.). The amino acid sequence data for 14 peptide fragments of gamma ependymin were derived in this way. All of these 14 peptide fragments correspond to identical sequences that were previously found for the ependymin molecule by Konigstorfer et al., *J. Neurochem.* 52:310–312 (1989). The gamma-chain sequence obtained by sequence analysis of the peptide digests of the gamma ependymin chain is identical to that reported for the beta form of the molecule reported by Konigstorfer et al., supra.

Searches for homologies between the ependymin peptide fragments produced by these methods and known polypeptides were carried out using the Protein Identification Resource of the National Biomedical Research Foundation (Roode, D. et al. *Nucl. Acids Res.* 16:1857–1859 (1988)) and the Swiss-Prot database at the University of Geneva.

Example 2. Effect of ependymin and ependymin fragments on nerve growth

Tissue Culture Assay System

A tissue culture system has been developed to serve as a bioassay for ependymin fragments. The assay is based on the fact that certain cholinergic and adrenergic cell lines have the capacity to grow neurites and establish connections resembling synapses in vitro. Normally, such cells require about 4–7 days of culture before 50–80% of them begin to show neurite growth. This process can be accelerated by addition of drugs such as cyclic adenosine monophosphate (cyclic AMP) to the culture medium.

Two cell lines were used. The mouse neuroblastoma cell line NB2a/dl was grown to confluency in P/100 plastic plates in the presence of Delbecco's medium with 10% fetal calf serum at 36.5° C. in a 5% $CO_2$ atmosphere. Shea, T. B. et al., *Dev. Brain Res.*, 21:307–314 (1985). An adrenergic mouse cell line based on PC12 pheochromocytoma cells was grown on collagen-coated culture plates using 85% RPMI 1640 and 10% heat-inactivated horse serum as the growth medium. Greene, L. A. et al., *Proc. Natl. Acad. Sci. USA*, 73:2424–2428 (1976). Cultures were grown in P-100 plates from an initial plating of $10^5$ cells/ml under sterile conditions using 10 ml of incubation medium. Experimental cultures received a given concentration of protein fragment in 1 ml of serum-free medium. Control cultures received no fragment. Equal numbers of test and control plates were incubated at 35.5° C. in a 95%/5% air/$CO_2$ humified atmosphere, and then examined for neurite growth patterns at 18, 24 and 48 hr after the plating in a phase microscope at a magnification of 100 or 200 ×, as specified.

1. Effect of the polypeptide ETLQFR (SEQ. I.D. No. 26) on promoting nerve growth The test was carried out blind to determine (1) the total number of cells present in a given field of observation (at 100×), (2) the percent of these that have one process and (3) the percent that have two or more processes. These three categories were determined in 5–7 randomly selected fields for each of two plates to obtain mean and standard deviation data for each group. The results for an average of 4 experimental plates (containing an additive) were compared to those for 4 controls grown from the same stock culture; 3 experimental and 3 controls, each of which was grown on the same 6-well plate. The pattern of neurite outgrowth was determined as a function of additive concentration and time. The data were used to calculate the percent of cells remaining undifferentiated, i.e., those with zero processes (0), the percent with one process (1+), and the percent with two or more neurite processes (2+).

The following additives were tested: pure ependymin, gamma-chain polypeptide and a control polypeptide. Ependymin was isolated from goldfish brain as previously described (V. E. Shashoua, *Neurochem. Res.* 13:649–655 (1988)). Briefly, this method comprises isolating an ependymin-rich protein fraction of brain extracellular fluid by extracting brain tissue for 30 minutes at 0° C. in a buffer consisting of sodium chloride, calcium acetate in Tris (pH 7.4) and L-1-tosylamide-2-phenylethylchloromethyl ketone as a protease and esterase inhibitor, V. E. Shashoua, *Neurochem. Res.* 6:1129–1147 (1981). Ependymin proteins are isolated and purified from this fraction by a combination of affinity chromatography, gel electrophoresis, and Sephadex-gel chromatography (Shashoua, V. E. *Brain Res.* 122:113–124 (1977)).

Gamma-chain peptide, initially isolated as a fragment from a trypsin digest of the gamma-chain of ependymin, was synthesized by the Merrifield process. It has the following sequence:

ETLQFR (SEQ. I.D. No. 26)

Control peptide was synthesized, with the following sequence:

KASTTTNYT (SEQ. I.D. No. 29)

All the test additives were dissolved in phosphate buffered saline, filter sterilized and stored as 1 mg/ml stock solutions.

The data were reproducible, irrespective of the number of cells present in a given field of observation. Statistical analysis using t-test comparisons of experimental vs. control cultures shows highly significant differences (p values of<0.0005).

Ependymin alone causes a rapid growth of neurites. Approximately 70% of the cells of untreated control cultures remain undifferentiated (round cells) at the end of 48 hr in culture. Identical cultures treated with 12.5 µg/ml (~$2\times10^{-7}$M) ependymin had only about 20% undifferentiated cells after 48 hr in culture. The one-process category of cells (1+) was the same for both control and the ependymin-treated cultures. However about 80% of treated cells with ependymin had two or more nerve processes (2+), a 4-fold increase over control. The data are statistically significant in a t-test analysis with a p value of less than 0.0005. This demonstrates that native protein ependymin can significantly promote neurite growth.

Figure 1:
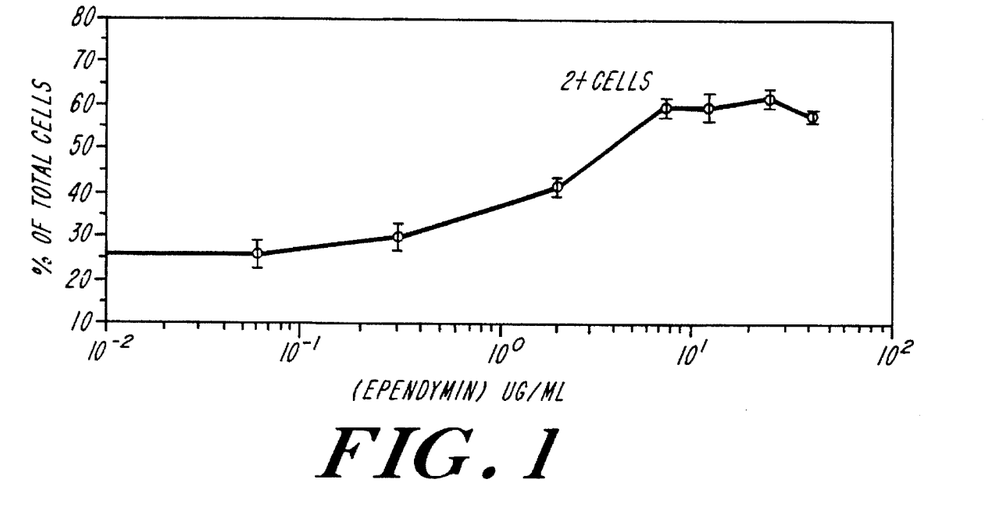
FIG. 1 is a graph showing the dose-response effect of whole ependymin on neurite growth of neuroblastoma cells.

FIG. 1 shows the dose-response data for effects of ependymin on the pattern of development of cells with two or more processes (2+) after 24 hr in culture. The data show that the half-maximal effective dose occurs at a concentration of about 2 µg/ml or $30\times10^{-9}$M. Also, there seems to be a plateau above a dose of 7.5 µg/ml, suggesting that there is a saturation of the response to the effects of ependymin. Thus, increased amounts beyond this level appear to cause no further enhancement of neurite growth.

A peptide fragment was isolated from tryptic digests of the molecule. This was found to correspond to a fragment of the molecule present at positions 78 to 85 in the sequence of the gamma-chain of ependymin. It is flanked by two N-terminal K (lysine) and one C-terminal R (arginine) in the sequence. It was synthesized as KKETLQFR (SEQ. I.D. No. 27) and used in assays, testing its capacity to potentiate growth of the neuroblastoma NB2a/dl cells in culture. The peptide has a molecular weight of 1034 and is highly soluble in saline at physiological pH values.

The polypeptide was highly effective in promoting neurite outgrowth. The effects of a dose of 2.5 µg/ml ($2.4 \times 10^{-9}$ M) revealed a reproducible and pronounced decrease in the number of undifferentiated cells (0 processes) and an increase in the number of cells with more than two processes (2+) with no change in the one-process category. The data for (0) and (2+) were statistically significant in a t-test comparison (p value of 0.0005) with those for untreated control cells. The effect of the polypeptide was readily observable after only 1–2 days in culture. The time course of development of type (2+) cells for a dose of 1.5 µg/mg of the peptide showed that within 24 hr, 60–80% of the cells plated developed neurites as compared to 20–30% in control plates. The results were highly reproducible. T-test comparisons vs. controls gave p values of 0.0005.

Figure 2:
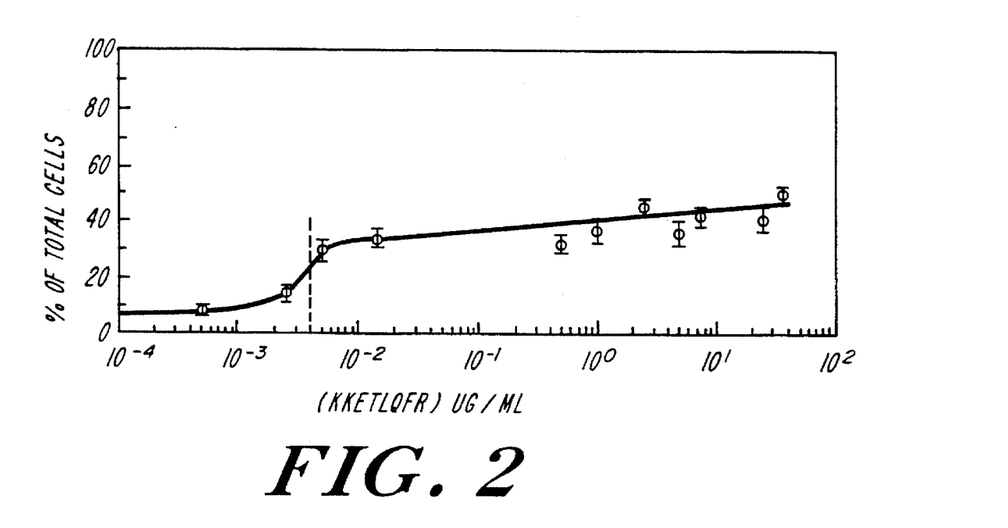
FIG. 2 is a graph showing the dose-response effect of a peptide fragment comprising the sequence KKETLQFR (SEQ. I.D. No. 27) on neurite growth of neuroblastoma cells.

FIG. 2 shows dose-response data for this polypeptide. There is an initial step function with a half-maximal effect of 0.004 µg/ml ($3.8 \times 10^{-9}$M) followed by a gradual linear increase as a function of concentration. If we calculate the ependymin equivalent by multiplying the half-maximal dose by the molecular weight ratios of native ependyminto KKETLQFR (SEQ. I.D. No. 27) (i.e., 68,000/1034) we find that the corresponding ependymin dose would be 0.263 µg/ml. This is a factor of about 10 less than the half-maximal dose for stimulating cell growth by pure ependymin (FIG. 1). Thus polypeptide KKETLQFR (SEQ. I.D. No. 27) appears to be 10-fold more active than ependymin itself.

Pretreatment of cells for a short period of time can induce a neurite outgrowth effect which persists after this polypeptide is removed from the culture. A series of experiments were performed in which cells were treated with 0.1 µg/ml of KKETLQFR (SEQ. I.D. No. 27) for 3 or 18 hr. The medium was then removed and replaced with control medium and the growth patterns of the cultures were examined after 24 and 48 hr in culture. The results showed that exposure for a 3-hr pulse of this polypeptide results in an enhanced growth which persists for 48 hr in comparison with controls. This suggests that this polypeptide might function as an initiation signal for neurite development.

The effect of this polypeptide does not appear to be due to an inhibition of protease activity. It is well established that inhibitors of proteases can promote the growth of neurites in culture (D. Monard, *Biochem. Pharm.* 36:1389–1392 (1987)). A comparison of the effect of this polypeptide at a dose of 1 µg/ml with a similar concentration of control was performed. In these experiments, the cultures were plated without any trypsin treatment to avoid effects that may arise from any residual proteases in the culture. The cells were washed in phosphate-buffered saline and grown for 24 hr. The results showed a clear increase in the (2+) type of cells with added KKETLQFR (SEQ. I.D. No. 27), whereas the data for those treated with a control peptide (KASTTTNYT) (SEQ. I.D. No. 29) are not significantly different from those of untreated controls.

2. Effect of secondary molecule-linked ependymin fragments on promoting nerve growth This Example illustrates that a prodrug comprising the polypeptide ETLQFR (SEQ. I.D. No. 26) linked to a secondary molecule is capable of promoting nerve growth with no toxic effects.

A. Synthesis of DHA Derivatives of 8933-KKETLQFR (SEQ. I.D. No. 27)

1. Synthesis of docosohexaenoic anhydride (DHA anhydride)

One gram of docosohexaenoic acid DHA (0.0003M) was dissolved in 100 ml of methylene chloride and 50 ml benzene. The mixture was stirred together with 0.36 g dicyclohexyl carbodiimide (DCC) for about 16 hours at room temperature. A white precipitate of dicyclohexyl urea formed. This was filtered off and the solution of the anhydride was then concentrated to a volume of 20 ml and refiltered to remove additional dicyclohexylurea. Aliquots of this solution were then used directly in the next stage of the synthesis.

2. Coupling of DHA anhydride with KKETLQFR (SEQ. I.D. No. 27) peptide

Ten milligrams of KKETLQFR (SEQ. I.D. No. 27) (MW 1034, $9.6 \times 10^{-6}$M) was dissolved in 10 ml of N-methylpyrrolidone containing 4.7 of N-dimethylamino pyridine (DMAP). A solution of the DHA anhydride ($9.6 \times 10^{-6}$M) in 0.14 ml benzene was then added and the mixture was stirred at room temperature for about 48 hours. The pale yellow solution was filtered and evaporated to dryness at 37° C. at reduced pressure (0.1 mm Hg). The product was then extracted 3× with 10 ml aliquots of hexane and then evaporated to dryness. The residue was dissolved in 5 ml of 1M acetic acid and extracted 3× with 10 ml aliquots of n-hexane followed by 3 additional extractions with 10 ml benzene to remove the DHA liberated in the reaction. The remaining solution was evaporated to dryness in a rotary evaporator to give a yellow viscous oil.

The product migrated as a single spot on a thin layer chromatogram as a compound with an Rf of 0.52 (KKETLQFR (SEQ. I.D. No. 27): Rf 0.25) using chloroform/methanol/acetic acid (77.5/15/7.5) as the elution solvent. The IR spectrum of the compound was consistent with the proposed mono-DHA derivative of the polypeptide. Strong absorption bands were found at: 3375, 3050, 1650, 1440, 1280, 1070, and 980 cm. The compound was water soluble.

A similar procedure was used to prepare the di-substituted DHA derivative of KKETLQFR (SEQ. I.D. No. 27). This had an Rf value of 0.9 on thin layer chromatograms using chloroform/methanol/acetic acid (77.5/15/7.5) as the solvent. Its IR spectrum was consistent with a di-substituted peptide. It was soluble in 70/30 ethanol/water.

B. Results

The tissue culture assay system used in this Example is identical to that described previously in Example 1. Gamma-chain peptide, initially isolated as a fragment from a trypsin digest of the gamma-chain of the ependymin was synthesized by the Merrifield process. It has the following sequence:

KKETLQFR (SEQ. I.D. No. 27)

The control peptide had the following sequence:

KASTTTNYT (SEQ. I.D. No. 29)

The mono, and di-docosahexaenoic acid derivatives of polypeptide KKETLQFR (SEQ. I.D. No. 27) were prepared as described above.

Figure 3A:
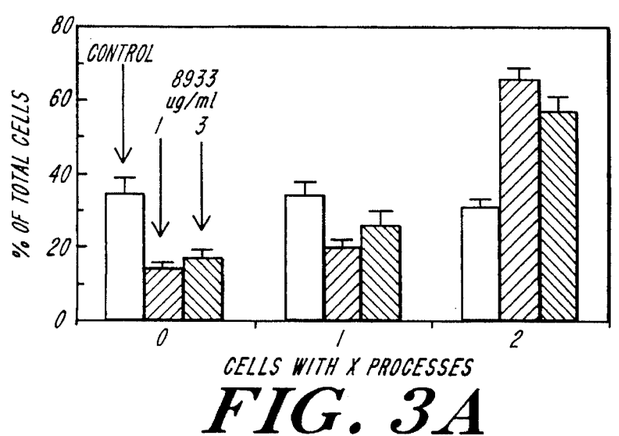
FIG. 3A shows the effect of KKETLQFR (SEQ. I.D. No. 27) on neurite growth.
Figure 3B:
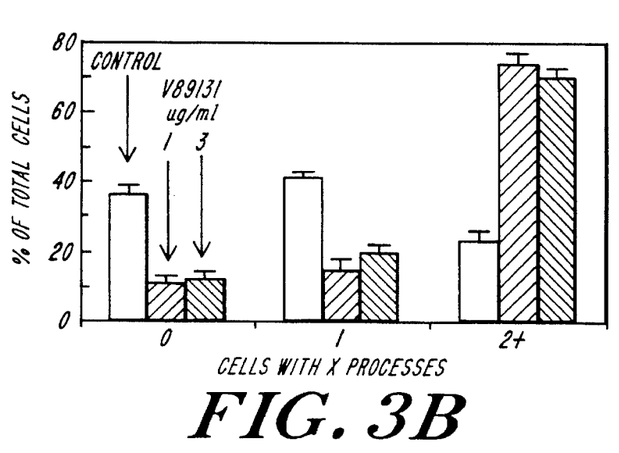
FIG. 3B shows the effect of the mono-docosohexaenoic acid derivative of KKETLQFR (V89–131) (SEQ. I.D. No. 27) on neurite growth.
Figure 3C:
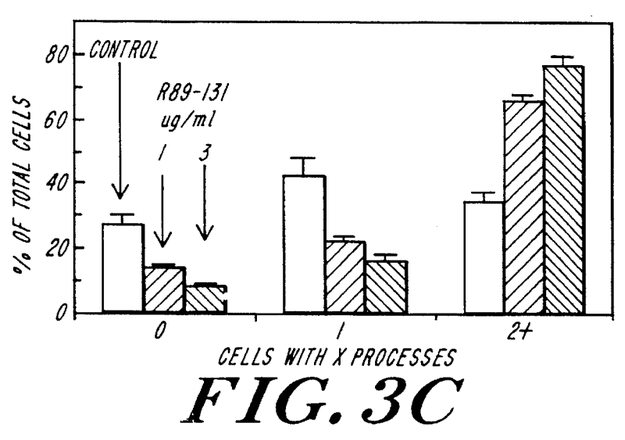
FIG. 3C shows the effect of the di-docosohexaenoic acid derivative of KKETLQFR (R89–131) (SEQ. I.D. No. 27) on neurite growth.

The polypeptide alone was highly effective in promoting neurite outgrowth. In a manner identical to that of Example 1, administration of this ependymin fragment produced a marked decrease in the number of undifferentiated cells (0 processes) and an increase in the number of cells of more than two processes (2+) (FIG. 3A). The effect of the mono-acid derivative of this polypeptide was even more pronounced (FIG. 3B). The effect of the di-docosahexaenoic acid derivative on neurite outgrowth was not significantly different from that of the polypeptide alone (FIG. 3C).

This Example illustrates that secondary molecules capable of crossing the blood-brain barrier can be coupled with polypeptides of this invention to yield prodrugs that are non-toxic. Moreover, such prodrugs can show greater nerve-growth promoting activity than the polypeptide alone.

3. Effect of nerve growth active regions (and substantially homologous regions) of ependymin The test to determine the degree of sprouting was carried out blind to determine (1) the total number of cells present in a given field of observation and (2) the percent of these that have zero and one or two or more process. Twelve microscope fields, each containing 50–100 cells, were randomly selected in each plate and cells counted according to the categories described above. The data for 12 fields in each of two plates for each added protein fragment were combined to obtain an analysis of the percent sprouting (i.e. the % of cells that have one or more processes after 24 hr in culture) for each protein fragment. The ratio, % sprouting in experimental cultures/% sprouting in control cultures, is an index of the "relative sprouting effect" (RSE) of a protein fragment. In the counting, a cell had a single, distinct process if that process had a minimum length equal to at least 0.5 times the cell body length.

In each of the twelve microscope fields, the length of nerve cell processes (minimum length: 0.5 times the cell body length) was also measured to determine the percentage of nerve elongation after 24 hr. The percentage of total cells that developed a longest process equal to its cell body length was calculated according to the formula in Table V, supra. The test protein fragments derived from gamma-ependymin and their sequences are sequence I.D. numbers 8, 15, 16, 17, and 18, supra. The following additives were also tested: pure ependymin, NGF and control protein fragment.

The gamma-chain fragments, some of which were initially isolated as the fragments from a trypsin digest of the gamma-chain of ependymin, as well as control fragments, were synthesized by the Merrifield process at the Peptide Synthesis Facility at Massachusetts General Hospital (Dr. G. Matsueda, Director). All the test additives were dissolved in phosphate buffered saline, filter sterilized and stored as 1 mg/ml stock solutions.

The data were reproducible, irrespective of the number of cells present in a given field of observation (Table III).

TABLE III

Neurite Sprouting Assay Data After 24 hrs in Culture

| Additive | NB2a/d1 cells | | PC12 cells | |
|---|---|---|---|---|
| | Conc. (μm) | RSE[a] | Conc. (μM) | RSE[a] |
| None | | 1.0 | — | 1.0 |
| Ependymin (Dimer-from goldfish brain) | 0.03 | 1.76 ± .04 | | |
| | 0.11 | 2.0 ± .03 | 0.11 | 2.2 |
| | 0.60 | 2.0 ± .03 | | |
| Nerve growth factor (7S-from mouse submaxillary gland) | 0.03 | 1.76 ± .034 | — | — |
| | .07 | 1.76 ± .07 | .07 | 2.9 |
| 8933[b] (Seq. ID No.: 27) | 0.1 | 1.3 ± .05 | 1.0 | 1.58 |
| | 1 | 1.6 ± .04 | | |
| | 4.8 | 2.0 ± .04 | | |

TABLE III-continued

Neurite Sprouting Assay Data After 24 hrs in Culture

| Additive | NB2a/d1 cells | | PC12 cells | |
|---|---|---|---|---|
| | Conc. (μm) | RSE[a] | Conc. (μM) | RSE[a] |
| I.D. No. 8 | 1.0 | 1.11 ± .04 | 0.9 | 1.7 |
| I.D. No. 15 | 1.0 | 1.1 ± .04 | 1.0 | 2.6 |
| I.D. No. 16 | | | 0.9 | 2.48 |
| I.D. No. 17 | 1.0 | 1.39 ± .05 | | |
| I.D. No. 18 | 0.5 | 1.5 ± .03 | | |
| I.D. No. 29 | 1.0 | 1.03 | 0.9 | 1.07 |
| dibutyryl cyclic AMP | 1000 | 1.7 | — | — |

[a]RSE = relative sprouting effect
= S with additive / S without additive
S = % of cells that have one or more processes after 24 hrs in culture
A process = a cell extension equal to 0.1 cell body length
[b]Sequence Lys Lys Glu Thr Leu Gln Phe Arg, described in co-pending application Ser. No. 07/517,159, filed May 1, 1990.

In experiments with two cell lines (Table III), whole ependymin can promote the sprouting of neurites in the neuroblastoma cell line (NB2a/dl) and in the pheochromocytoma cell line (PC12).

Whole ependymin has comparable properties to nerve growth factor (NGF) in terms of initiating neurite sprouting. Specific fragments of the gamma-chain of ependymin have similar properties. Fragments with sequence I.D. Nos 15 and 16 both correspond to amino acid residues of the gamma ependymin chain that are substantially homologous to a portion of nerve growth factor. Measurements in the pheochromocytoma cell cultures show that both fragments could promote neurite sprouting. The concentrations for inducing neurite sprouting appear to be 10–15 fold higher than those required for intact nerve growth factor and intact ependymin. It is worth noting that both fragments were effective on the PC12 cells but had no significant effect on the neuroblastoma cells. Other fragments such as sequence I.D. Nos. 8, 17, and 18 are fragments of the gamma-chain of ependymin that are associated with the matrix-promoting neuroactive domains of the ependymin molecule (see Table I). These fragments were less effective in promoting neurite sprouting than the fragments from the nerve growth neuroactive domain (see Table II).

In an analogous manner, whole nerve growth factor had the most significant effects on neurite elongation (Table IV). Fragments substantially homologous to the nerve growth neuroactive domain were similarly less effective in the neuroblastoma cell culture than in the PC12 cell culture, in terms of their effect on neurite elongation.

TABLE IV

Neurite Elongation Assay Data After 24 hrs in culture

| Additive | NB2a/d1 cells | | PC12 cells | |
|---|---|---|---|---|
| | Conc. (μM) | REE[a] | Conc. (μM) | REE[a] |
| None | — | 1.0 | — | 1.0 |
| Ependymin | — | — | .03 | 1.74 |
| Nerve Growth Factor | — | — | .03 | 3.30 |
| 8933[b] (Seq. ID No.: 27) | — | — | 0.9 | 1.45 |
| I.D. No. 8 | 0.9 | 1.47 | 0.9 | 1.72 |
| I.D. No. 15 | — | — | 0.9 | 2.64 |
| I.D. No. 16 | — | — | 0.2 | 2.18 |

TABLE IV-continued

Neurite Elongation Assay Data
After 24 hrs in culture

| | NB2a/dl cells | | PC12 cells | |
|---|---|---|---|---|
| Additive | Conc. (μM) | REE[a] | Conc. (μM) | REE[a] |
| I.D. No. 17 | 0.7 | 1.48 | 0.2 | 2.18 |
| I.D. No. 18 | 0.5 | 1.80 | 0.5 | 1.55 |
| dibutyryl cAMP | 1000 | 2.58 | | |

[a]REE = relative elongation effect
$= \dfrac{E \text{ with additive}}{E \text{ without additive}}$
$E = \Sigma\ x_1 l_1 + x_2 l_2 + x_3 l_3 \ldots + x_n l_n$
where:
$x_1$ = % of cells that have a process = one body length ($l_1$)
$x_2$ = % of cells that have a process = two body length ($l_2$)
$x_n$ = % of cells that develop a longest process equal to n cell body lengths
[b]Sequence Lys Lys Glu Thr Leu Gln Phe Arg, described in co-pending application Ser. No. 07/517,159, filed May 1, 1990.

The molecules of this invention including ependymin fragments that are substantially homologous to an active region of a neuroactive ependymin domain, may be useful as treatments to enhance recovery after stroke, as a factor that promotes neurite outgrowth and regeneration. These molecules might be useful in enhancing long term memory capacity that is lost during the normal process of aging. Thus, molecules of this invention may restore the aging-related decline in capacity of brain cells to form new connections.

Molecules of this invention can also be useful in treatment in brain degenerative processes to promote the formation of neuronal connections broken during the onset and development of Huntington's, Parkinson's and Alzheimer's diseases. Molecules of this invention may also be useful in studies of transplantation of neurons. Pre-treatment of neurons with these protein fragments or transplantation in the presence of the protein fragments may enhance connectivity and growth.

Equivalents

Those skilled in the art will recognize, or be able to ascertain using no more than routine experimentations, many equivalents to the specific embodiments of the invention described herein. Such equivalents are intended to be encompassed in the scope of the following claims.

I claim:

1. An isolated peptide selected from the group consisting of Sequence I.D. Numbers 1–27 and 28.

2. The isolated peptide of claim 1, further comprising at least two adjacent basic amino acids linked directly to at least one end thereof, said at least one end selected from the group consisting of the N-terminal end and the C-terminal end.

3. The isolated peptide of claim 2, further comprising a pharmaceutically acceptable secondary molecule coupled to the at least two adjacent basic amino acids, wherein the pharmaceutically acceptable secondary molecule is a fatty acid having between about 16 and about 22 carbon atoms.

4. The isolated peptide of claim 3, wherein the pharmaceutically acceptable secondary molecule coupled to the at least two adjacent basic amino acids of the isolated peptide has a brain-penetration index at least twice that of the isolated peptide which is not coupled to the pharmaceutically acceptable secondary molecule.

5. The isolated peptide of claim 3, wherein the peptide is selected from the group consisting of Sequence I.D. numbers 26, 27, and 28.

6. The isolated peptide of claim 1, wherein the peptide is selected from the group consisting of SEQ. I.D. Nos. 1, 8, 11, 14, 15, 16, 17, 18, 21, 22, 25, 26, 27 and 28.

7. The isolated peptide of claim 6, wherein the peptide is selected from the group consisting of SEQ. I.D. Nos. 8, 15, 16, 17, 18 and 27.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:1:

Asp  Leu  Gln  Val  Phe  Val
    1                      5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:2:

Gly  Glu  Lys  Lys  Asp
    1                    5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:3:

Ala Thr His Glu Ser
1               5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:4:

Cys Leu Pro Val Ser Gly
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:5:

Leu Pro Val Ser Gly Ser
1               5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:6:

Pro Cys His Ala Pro Pro
1               5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:7:

Gly Gly His Asp Leu Glu Ser Gly
1               5

( 2 ) INFORMATION FOR SEQ ID NO:8:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:8:

Asp  Asp  Leu  Gln  Val  Phe
1                  5

( 2 ) INFORMATION FOR SEQ ID NO:9:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:9:

Pro  Leu  Thr  Ser  Gly
1                  5

( 2 ) INFORMATION FOR SEQ ID NO:10:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:10:

Leu  Ile  His  Phe  Glu  Glu  Gly  Val
1                  5

( 2 ) INFORMATION FOR SEQ ID NO:11:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:11:

Gly  Glu  Phe  Ser  Tyr  Asp  Ser
1                  5

( 2 ) INFORMATION FOR SEQ ID NO:12:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:12:

His Ala Pro Pro Leu Thr Ser
1               5

( 2 ) INFORMATION FOR SEQ ID NO:13:

( i ) SEQUENCE CHARACTERISTICS:
       ( A ) LENGTH: 7 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:13:

Asp Leu Glu Ser Gly Glu Phe
1               5

( 2 ) INFORMATION FOR SEQ ID NO:14:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:14:

Gly Glu Phe Ser Val Cys Asp Ser
1               5

( 2 ) INFORMATION FOR SEQ ID NO:15:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:15:

Lys Lys Gly Glu Phe Ser Val Ala Asp Ser
1               5                   10

( 2 ) INFORMATION FOR SEQ ID NO:16:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:16:

Lys Lys Gly Glu Phe Tyr Cys Ser Arg
1               5

( 2 ) INFORMATION FOR SEQ ID NO:17:

( i ) SEQUENCE CHARACTERISTICS:
       ( A ) LENGTH: 13 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:17:

```
Gly Leu Arg Val Arg Val Trp Asn Gly Lys Phe Pro Lys
1               5                   10
```

( 2 ) INFORMATION FOR SEQ ID NO:18:

( i ) SEQUENCE CHARACTERISTICS:
        ( A ) LENGTH: 16 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:18:

```
Gly Val Ala Phe Glu Glu Ala Pro Asp Asp His Ser Phe Phe Leu Phe
1               5                   10                  15
```

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:19:

```
Gly Gly His Asp Leu Ser Gly
1               5
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:20:

```
Gly Gly His Asp Leu Glu Ser Gly
1               5
```

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:21:

```
Gly Gly His Asp Leu Glu Ser Gly Glu Phe Ser Tyr Asp Ser
1               5                   10
```

( 2 ) INFORMATION FOR SEQ ID NO:22:

( i ) SEQUENCE CHARACTERISTICS:

( A ) LENGTH: 14 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:22:

Gly Gly Ser Asp Leu Ser Gly Glu Phe Ser Val Cys Asp Ser
1               5                   10

( 2 ) INFORMATION FOR SEQ ID NO:23:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:23:

Gly Gly Ser Asp Leu Ser Gly Gly Glu Phe Ser Val Cys Asp Ser
1               5                   10                  15

( 2 ) INFORMATION FOR SEQ ID NO:24:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:24:

Gly Gly Ser Asp Leu Ser Gly Gly Glu Phe Ser Val Ala Asp Ser
1               5                   10                  15

( 2 ) INFORMATION FOR SEQ ID NO:25:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:25:

Gly Gly Ser Asp Leu Ser Gly Glu Phe Ser Val Ala Asp Ser
1               5                   10

( 2 ) INFORMATION FOR SEQ ID NO:26:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:26:

Glu Thr Leu Gln Phe Arg
1               5

(2) INFORMATION FOR SEQ ID NO:27:

(i) SEQUENCE CHARACTERISTICS:
(A) LENGTH: 8 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:27:

Lys Lys Glu Thr Leu Gln Phe Arg
1               5

(2) INFORMATION FOR SEQ ID NO:28:

(i) SEQUENCE CHARACTERISTICS:
(A) LENGTH: 8 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:28:

Glu Thr Leu Gln Phe Arg Lys Lys
1               5

(2) INFORMATION FOR SEQ ID NO:29:

(i) SEQUENCE CHARACTERISTICS:
(A) LENGTH: 9 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:29:

Lys Ala Ser Thr Thr Thr Asn Tyr Thr
1               5